United States Patent [19]

Gertzbein et al.

[11] Patent Number: 5,620,443
[45] Date of Patent: Apr. 15, 1997

[54] ANTERIOR SCREW-ROD CONNECTOR

[75] Inventors: Stanley Gertzbein, Houston, Tex.;
Michael C. Sherman, Memphis, Tenn.

[73] Assignee: Danek Medical, Inc., Memphis, Tenn.

[21] Appl. No.: 377,658

[22] Filed: Jan. 25, 1995

[51] Int. Cl.$^6$ .................................................. A61B 17/70
[52] U.S. Cl. .............................................. 606/61; 606/73
[58] Field of Search .................... 606/61, 60, 72, 606/73, 74, 57, 105; 623/17, 16

[56] References Cited

U.S. PATENT DOCUMENTS

| | | | |
|---|---|---|---|
| 3,741,205 | 6/1973 | Markolf et al. | 128/92 |
| 4,611,581 | 9/1986 | Steffee | 128/69 |
| 4,653,481 | 3/1987 | Howland et al. | 606/61 X |
| 4,719,905 | 1/1988 | Steffee | 606/61 X |
| 4,773,402 | 9/1988 | Asher et al. | 606/61 X |
| 5,024,213 | 6/1991 | Asher et al. | 606/61 X |
| 5,085,660 | 2/1992 | Lin | 606/73 |
| 5,108,395 | 4/1992 | Laurain | 606/61 |
| 5,112,332 | 5/1992 | Cozad et al. | 606/61 |
| 5,129,899 | 7/1992 | Small et al. | 606/61 |
| 5,147,361 | 9/1992 | Ojima et al. | 606/61 |
| 5,261,909 | 11/1993 | Sutterlin et al. | 606/61 |
| 5,306,275 | 4/1994 | Bryan | 606/61 |
| 5,324,290 | 6/1994 | Zdeblick et al. | 606/61 |
| 5,380,325 | 1/1995 | Lahille et al. | 606/61 |

OTHER PUBLICATIONS

*Spinal Product Systems*, Zimmer (Brochure) date and author unknown, pp. 29–33.

TSRH™ *Spinal Implant System* –Danek Medical (Brochure), date and author unknown, 3 pages.

*Kaneda Anterior Spinal Instrumentation System*, AcroMed Corp. (Brochure), date and author unknown, 6 pages.

*Stafix Plate System*, Daruma (Brochure), date and author unknown, 2 pages.

CASF™ *Contoured Anterior Spinal Fixation System*, AcroMed Corp. date and author unknown, 1 page.

*The Syracusel–Plate*, Bayley, Yuan, Fredrickson, Spine, vol., No. 3 Supplement, 1991, 5 pages.

*Primary Examiner*—Guy V. Tucker
*Attorney, Agent, or Firm*—Woodard, Emhardt, Naughton, Moriarty & McNett

[57] ABSTRACT

A transverse fixator assembly for spanning between a number of longitudinal members situated adjacent a patient's vertebrae and methods for fixation of the spine which allow variation of the distance between two or more vertebrae. The assembly includes a number of connectors configured to span the distance between and engage the longitudinal members. The connectors define a thru-hole for engaging a bone bolt which is engaged to a vertebra plus a number of spikes projecting from the connector. A locking mechanism is configured to prevent the bolt from rotating relative to the connector when the nut is being tightened. One or more of the connectors may be a dynamic connector which is slidably engaged to the longitudinal members to vary the distance between the vertebrae for compression or distraction.

13 Claims, 4 Drawing Sheets

ANTERIOR SCREW-ROD CONNECTOR

FIELD OF THE INVENTION

The present invention broadly concerns devices for use in spinal implant systems, particularly those using spinal rods contoured for connection at various locations along the length of the spinal column. More specifically, the invention concerns an apparatus for spanning between spinal rods to support vertebral fixation elements of the implant system which provide direct engagement to vertebrae of the spinal column. The invention is particularly useful with methods and devices for anterior fixation of the spine.

BACKGROUND OF THE INVENTION

Spinal fractures often occur at the thoracolumbar junction. Most of these fractures are burst injuries which are particularly dangerous because retropulsed bone fragments can cause spinal cord or caudal equina injuries. Posterior fixation has long been the primary approach for traumatic spinal injuries of this type.

The development of posterior internal fixation procedures for burst fractures was a substantial improvement over early approaches of bed rest and body casts. However, several disadvantages to these procedures were discovered. For example, this approach fails to reduce kyphosis or allow complete clearing of the spinal canal. Other complications include pseudoarthroses, late rod disengagement and inadequate reduction. Also, some posterior instrumentations require the fusion to extend at least two levels above and below the injury, particularly at the thoracolumbar junction. The posterior approach is also limited in the viability for use in burst fractures because in such fractures neural compression generally occurs from the anterior direction. Therefore, it is better to decompress and fuse the spine anteriorly. These difficulties have motivated attempts at anterior approaches. Various anterior and posterior spinal fixation devices and methods are discussed in Howard S. An, et al., (1992) *Spinal Instrumention*, herein incorporated by reference.

There are several advantages to anterior internal fixation. An anterior approach allows complete clearance from the spinal canal of bone fragments and/or total resection of a tumor. It also permits fusion of a minimal number of motion segments. In spite of these advantages, the use of anterior approaches has been limited by the risk of complications and other disadvantages of current systems.

Several plate and screw systems have been designed for anterior instrumentation of the spinal column. The Syracuse I-Plate (Danek and Synthes) may use rigid or semi-rigid screws in combination with a plate. Distraction or compression of the bone graft is not possible with this system. The CASF Plate marketed by Acromed is designed to be used in a semi-rigid manner. This device, as well, does not permit compression or distraction of the bone graft and in addition cannot be used in a rigid construct. The Stafix Plating System marketed by Daruma of Taipei, Taiwan, is an anterior thoracolumbar plate designed to address similar indications. This plate incorporates slots and holes as well as permitting quadrilateral placement of screws. The Anterior Thoracolumbar Plating System under development with Danek and Dr. Zdeblick is a slotted plate designed to attach to the anterior lateral aspect of the vertebral body. The plate allows distraction and/or compression through the use of two screws and two bolts.

Several modular spinal instrumentation systems were developed for anterior instrumentation. The Kaneda device is a system which includes a rod coupler distant from the point of attachment to the vertebral bodies. Rods are inserted through holes in the spinal screw heads which are then attached to the superior and inferior vertebral bodies. Normally two screws are placed in each body, therefore two rods are required. These rods are threaded to allow compression and distraction and are connected to form a solid construct at the end of the procedure. The Texas Scottish Rite Hospital System is also a modular spinal system which can be used anterioraly for the management for burst fractures or tumors. This device can be configured much in the same way as the Kaneda device with two screws in the superior and inferior vertebral body, each connected by rods which are in turn connected together. The Dunn device is another anterior spinal fixation device for use in tumor or thoracolumbar burst fractures. This device, similar to Kaneda, involves vertebral body staples, screws positioned in the vertebral body, and two threaded rods connecting a superior and inferior vertebral body to form a rigid construct.

These systems have proved unsatisfactory. Many of these devices such as the Syracuse I-plate and the Casp plate do not allow distraction or compression of a bone graft in fusion cases. Such static systems cannot be used to correct certain disorders such as kyphosis. The systems that do allow distraction and/or compression are often too complicated and involve the use of multiple screws and bolts. The prominent bone screws and rods of some devices increase the danger of vascular injury. Hardware failures, such a screw pull-out, have led to complications, including pseudoarthrosis. Some systems are further limited because they cannot be used in a rigid construct.

It would therefore be desirable to have a low profile, streamlined system with a minimum of separately implanted components to reduce the amount of time required to implant the system, the risk of vascular injury and the problem of irritation to the surrounding soft tissue of the patient.

A need exists for devices for anterior fixation which reduce the risks of anterior fixation by providing a mechanism to prevent hardware failures, such as screw pull-out.

It is desirable to have a spinal fixation system that is readily adapted to provide lateral coupling between spinal rods and multiple stages or segments of the spinal column. Such a system should provide this segmental interconnection without interfering with vertebral areas available for bone grafting to achieve permanent fixation or immobilization of damaged vertebrae.

There is also a need for low profile, streamlined systems which allow variation of the distances between vertebrae, i.e., compression and distraction, without the need for complicated instrumentation and tools.

There is currently no system that addresses each of these features in a single apparatus. The present invention addresses these needs and provides other benefits not previously found in spinal fixation systems of the prior art.

SUMMARY OF THE INVENTION

In accordance with the invention, an apparatus is provided for spanning between a pair of longitudinal members situated adjacent a patient's vertebrae along the sagittal plane. The assembly includes a number of connectors which are engageable to the longitudinal members via clamping surfaces provided in a slot defined in the connector. Each of the connectors defines a thru-hole for engaging a bone bolt which in turn is engaged to a vertebral body. A fastener clamps the bone bolt to the connector. The assembly also includes a number of fixation spikes projecting from the connector which are configured to engage the vertebrae.

In a specific embodiment of the invention, there is provided a locking mechanism configured to prevent the bolt from rotating relative to the connector and the vertebra when the nut is being tightened. The locking mechanism may include radial splines on the lower surface of the connector and also on a mating face on the bone bolt. In another embodiment, the spinal fixation system includes a dynamic, or movable, rod connector and a fixed rod connector which allows variation of the distances between vertebrae for compression or distraction.

One object of the invention is to provide an apparatus for use in laterally connecting longitudinal members implanted adjacent a patient's vertebral column.

Another object of this invention is to provide an apparatus which provides for convenient management of thoracolumbar burst fractures and tumors and which permits anterior load sharing as well as compression and distraction.

One benefit of the apparatus of the present invention is that it combines means for connecting the vertebral fixation elements to the spinal rods with means for laterally or transversely connecting the spinal rods together. An additional benefit is that the invention provides a more compact construct with a lower profile as compared to prior spinal rod constructs employing many individual components to connect vertebrae and spinal rods.

Yet another benefit achieved by the invention resides in providing segmental coupling or connection of the spinal rods, while permitting a wide variation of orientations at the vertebral fixation elements relative to the spinal rods.

Another advantage of this invention is that it provides fixation assemblies that can be top loaded, or implanted over bolts after the bolts have been engaged in the vertebrae.

Other objects and further benefits of the present invention will become apparent to persons of ordinary skill in the art from the following written description and accompanying figures.

DESCRIPTION OF THE PREFERRED EMBODIMENTS

Figure 1:
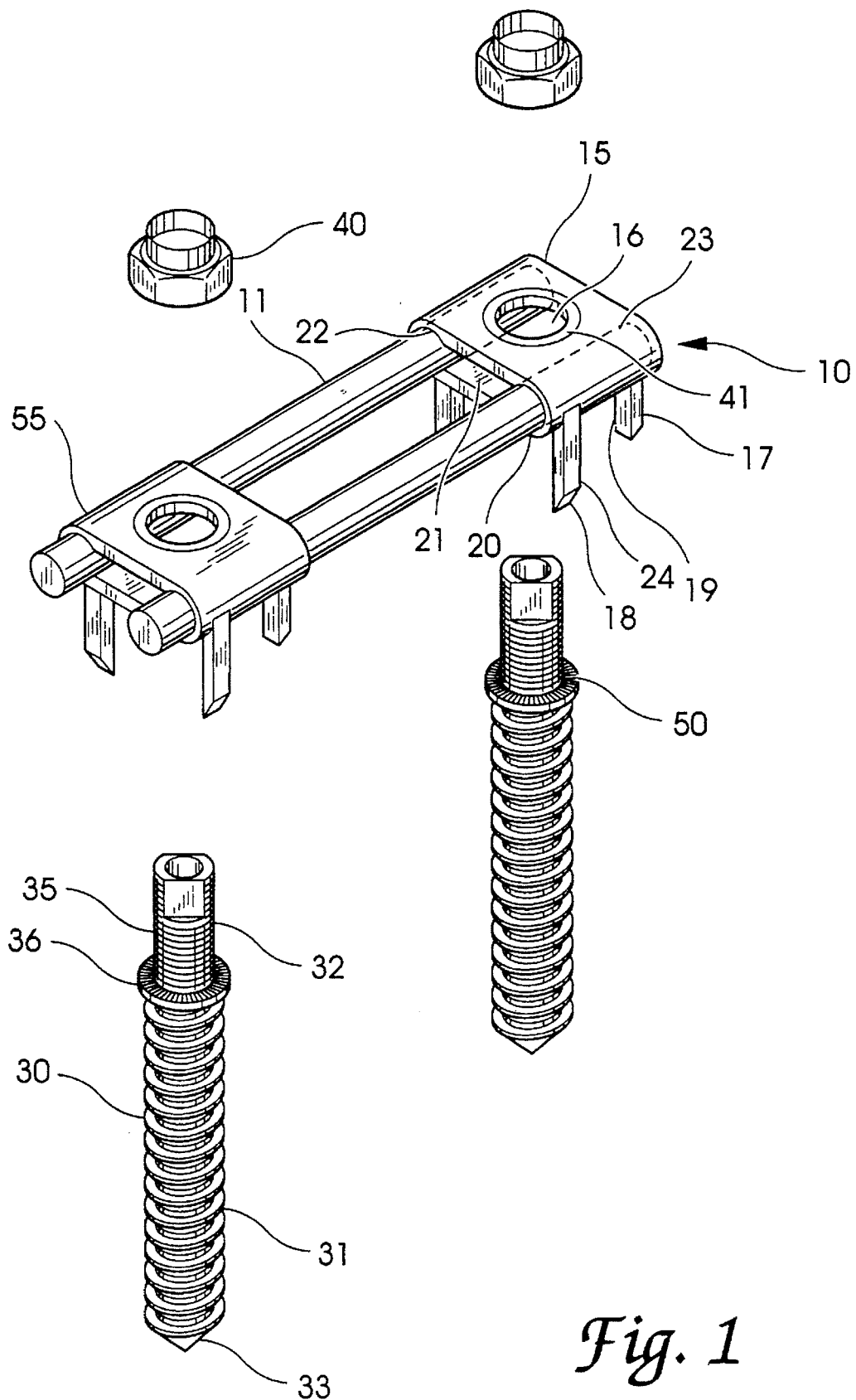
FIG. 1 is an exploded perspective view of the spinal fixation system of the present invention including a pair of transverse connectors spanning between two spinal rods with a pair of vertebral fixation bolts and corresponding nuts.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

The present invention is useful for anterior internal fixation of the spine which is indicated for thoracolumbar burst fractures with significant canal compromise, vertebral body tumors, lesions due to infection, spondylolisthesis, degenerative discs, and post-laminectomy instability.

This invention provides a top-loaded, low profile anterior fixation system which requires minimal instrumentation yet permits anterior load sharing and compression or distraction. The unique constructs of this invention permit fixation and compression or distraction with only two bolts, two rods and two rod connectors.

A spinal fixation system 10 in accordance with a preferred embodiment of the present invention is depicted in FIG. 1. The system 10 includes a transverse connector 15 defining a thru-hole 16 and having a lower bone engagement surface 20 and an upper surface 23. The transverse connector 15 engages a number of longitudinal members 11 by clamping surface 22 provided in a slot 21 defined in the connector 15. Preferably the longitudinal members 11 are spinal fixation rods. In one embodiment, the members 11 are smooth shot peened rods.

Figure 2:
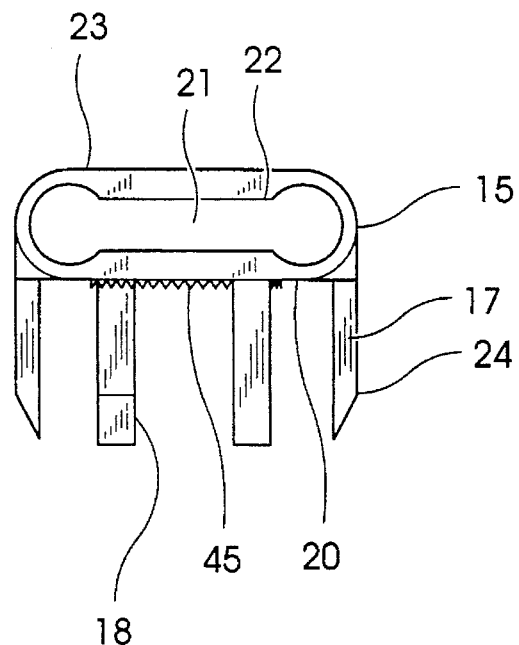
FIG. 2 is an end elevational view of a transverse connector according to one embodiment.
Figure 3:
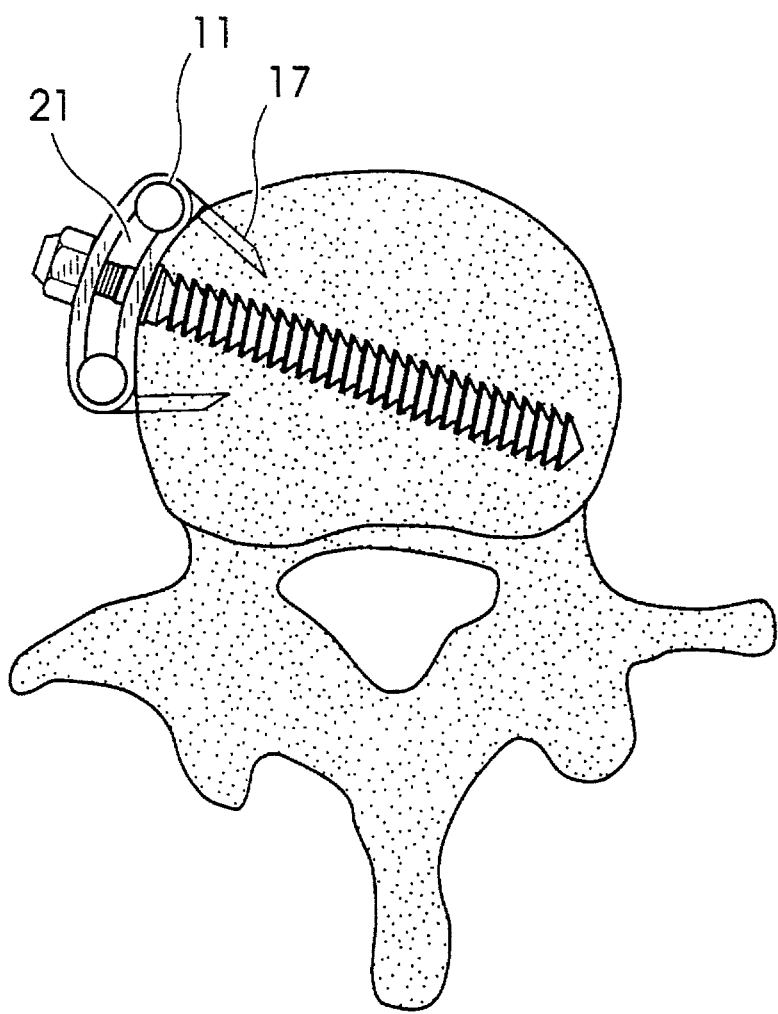
FIG. 3, is a side cross-sectional view of a transverse connector engaged to a vertebra.

Referring to FIGS. 1, 2, and 3, a number of fixation spikes 17 are fixedly attached to the lower surface 20 of the connector 15. The lower surface 20 of the connector 15 in combination with an inner surface 19 of the fixation spikes 17 are configured to fit snugly around either side of a vertebra. In another application, the fixation spikes 17 may be slightly embedded into the vertebra. The end of each spike 17 is preferably beveled on its outer surface 24 so that each fixation spike 17 terminates in a wedge shape 18 which may aid in fixing and holding the connector 15 in place over a vertebra.

Figure 4:
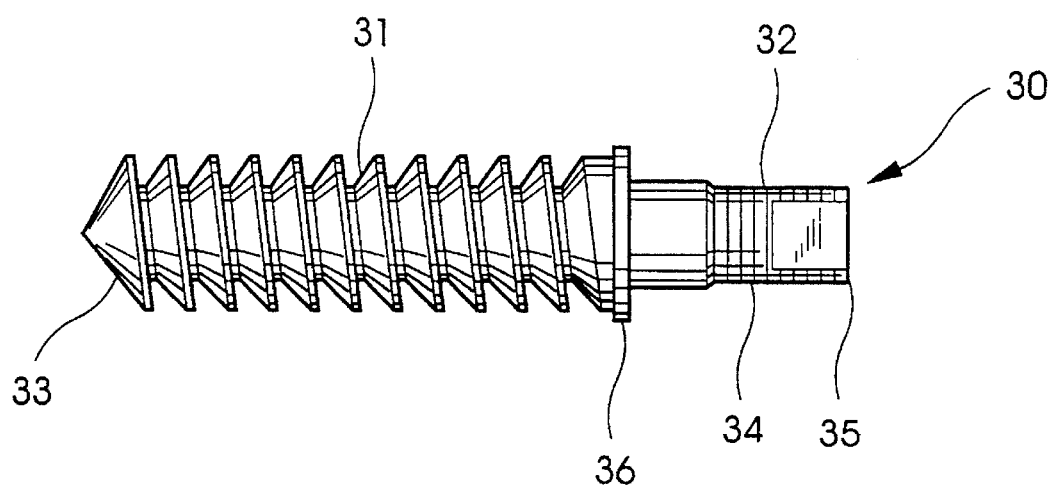
FIG. 4 is a side elevational view of a bone bolt according to one embodiment of the invention for use with the fixation system shown in FIG. 1.

Bolts 30 are used to attach the system 10 to the vertebrae. It is understood that "bolt" refers to any of various bone fasteners, including a standard bone screw. The present invention is unique because it requires only one bolt per connector. Previous devices have required two. FIG. 4 shows one embodiment of a bolt 30 in detail. The bolt 30 has a vertebra engaging portion 31 at a first end 33 and a post 32 at a second end 35. The vertebra engaging portion 31 of the bolt 30 may be configured, for example, with cancellous threads for fixation in the spongy bone of the vertebral body. The bolt also includes an integral flange 36 for supporting and clamping the connector 15. In one embodiment, the second end 35 is configured to receive a driving tool. The configuration may include an internal or external hex as is well known in the art.

The fixation system 10 can be top-loaded, i.e., implanted over a bolt 30 after the bolt 30 is engaged to a vertebra. This is advantageous because it reduces the required size of the surgical opening and trauma to the patient. Top-loading also provides a mechanical advantage during implantation of the system. After a bolt 30 is engaged to a vertebra by conventional means, the post 32 is insertable through the thru-hole 16 of the connector 15. A fastener 40 is provided for each of the bolts 30. The fastener 40 engages to the post 32 of the bolt 30 to secure the connector 15 to the bolt 30 and to clamp the longitudinal members 11 within the slot 21 of the connector 15. Thus, the longitudinal members 11 and the connector 15 are secured by a single bolt 30. Where the fastener 40 is a threaded nut, as in the preferred embodiment, the post 32 of the bolt 30 may included machine threads to engage with the nut. The nut or other fastener 40 is then top-tightened with a tool such as a socket wrench.

The connector 15 may define recesses 41 surrounding each thru-hole 16 defined in the connector 15. Each recess can be configured to accept a fastener 40 in low profile so that the fastener 40 does not extend over the upper surface 23 of the cormhector 15 when it is engaged to a posts 32. The recesses 41 can be concave to accept an arcuate underside of the fastener 40.

Figure 5:
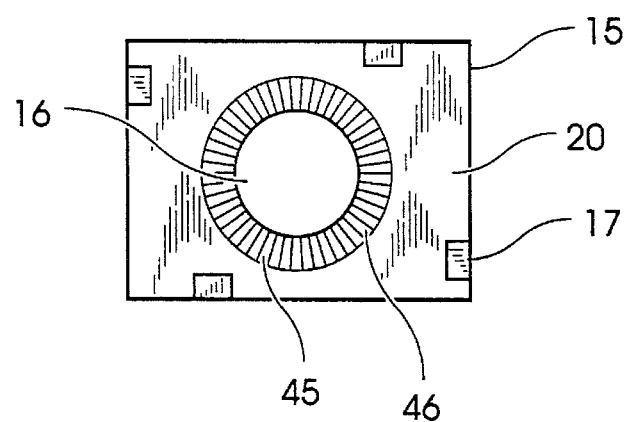
FIG. 5 is a bottom elevational view of the lower surface of a transverse connector shown in FIG. 1.
Figure 6:
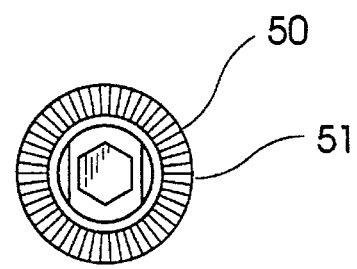
FIG. 6 is a top elevational view of the bone bolt according to one embodiment as shown in FIG. 2.

The spinal fixation system 10 may also be provided with a locking mechanism configured to prevent the bolts 30 from rotating relative to the connector 15 and the vertebra when the fastener or nut 40 is being tightened onto the bolt 30. The locking mechanism also prevents tile bolts from pulling out over time. In one embodiment of the invention, the locking mechanism includes an annular ring 45 defined on the lower surface 20 (FIG. 5) of the connector 15 and a mating face 50 affixed to each bolt 30 at a location between the post 32 and the vertebrae engaging portion 31. The annular ring 45 on the lower surface 20 of the connector 15 is concentrically disposed around the thru-hole 16 and includes a number of radial splines 46. Referring to FIGS. 1 and 6, the mating face 50 is concentrically disposed around and affixed to the bolt 30 and includes a number of opposing radial splines 51 for interdigitated engagement with the radial splines 46 on the lower surface 20 of the connector 15. The annular ring 45 may alternately be a washer affixed to or a ring integrally formed on the lower surface 20 of the connector 15.

The clamping surface 22 provided by the slot 21 defined in the connector 15 may include a number of scallops (FIG. 6). The scallops are configured to receive the longitudinal members 11 in a manner that is well known in the art. For example, each scallop can be generally formed at a radius that is slightly smaller than the radius of the longitudinal member 11 which is to be situated within the scallop. The scallops provide means for fixing the spinal rods so that the longitudinal members 11 and connector 15 do not shift relative to each other. However, it is understood that the slot 21 defined in the connector 15 may be smooth and that other means may be provided to firmly fix the longitudinal members 11.

For example, in one embodiment, the slot 21 is smooth and the engagement of the longitudinal members 11 with the connector 15 is secured by a clamping action. The tightening of a fastener 40 on the post 32 causes a narrowing of the slot 21 of the connector 15 which in turn causes the connector 15 to securely clamp the longitudinal members 11.

Another aspect of this invention provides means to vary the distance between vertebral bodies. According to the invention, a dynamic transverse connector 55 (FIG. 1) is slidable along the two longitudinal members 11 for compression and distraction of the vertebral bodies attached to the system 10. One or more of other connectors 15 may be engaged to the longitudinal members at a fixed location. After compression or distraction is achieved, the dynamic connector 55 can be fixed by tightening the bolt 30 to which the connector 55 is fastened. The nuts 40 which attach to the bolts 30 can then be top tightened with a tool such as a socket wrench.

The invention also provides methods for fixating the spine which include drilling a first hole in a first vertebral body and drilling a second hole in a second vertebral body. A bone bolt 30 is engaged to each of the first and second holes. The vertebrae are then supported with a fixation system 10 which includes two longitudinal members 11, such as rods. A first connector 15 is attached to a first end of each of the longitudinal members 11, and a dynamic rod connector 55 is slidably engaged to the longitudinal members 11. One of the bone bolts 30 is engaged to the thru-hole 16 of the first connector 15. The dynamic rod connector 55 is situated so that another bolt 30 engages a thru-hole 16 in the dynamic rod connector 55. The dynamic rod connector 55 is then slid along the longitudinal members 11 to vary the distance between the first and second vertebrae. The post 32 of each bone bolt 30 is then engaged with a nut 40 to secure the fixation system 10 to the vertebrae. The dynamic rod connector 55 may be slid along the longitudinal members 11 in the direction towards the fixed connector 15 to compress the vertebrae before engaging the bone bolts 30 with the nuts 40. The dynamic connector 55 may also be slid in a direction away from the fixed connector for distraction.

The spinal fixation system 10 is preferably formed of medical grade stainless steel or similar high strength material. Other materials are contemplated, provided the material is strong enough to endure the high loads transmitted through the components, and yet are biocompatible. Specifically, the system could be manufactured in 6A14V titanium or 316LVM stainless steel. The system can be provided in several different sizes ranging from, but not limited to, 2.0 inches to 5.5 inches.

While the invention has been illustrated and described in detail and the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A spinal fixation system comprising:
   at least two longitudinal members;
   a transverse connector defining a thru-hole and having
      a lower bone engagement surface,
      an opposite upper surface, and
      said connector defining a slot to receive said members, and a number of internal clamping surfaces surrounding said slot, said clamping surfaces configured to engage said members;
   a number of spikes projecting from said lower surface of said connector, said spikes configured to engage a vertebra;
   a bolt having
      a vertebra engaging portion on a first end,
      a post on a second end, said post insertable through said thru-hole of said connector,
      an integral flange between said vertebra engaging portion and said post for suppporting said connector;
   a fastener engageable to the post of said bolt to secure the connector to the bolt and to clamp said connector between said fastener and said flange of said bolt; and
   a locking mechanism configured to prevent the bolt from rotating relative to said connector and vertebra when the threaded nut is threaded onto said post.

2. The system of claim 1 wherein said locking mechanism includes:
   an annular ring defined on the lower surface of said connector and concentrically disposed around the thru-hole, said annular ring defining a number of radial splines; and a mating face affixed to said flange and concentrically disposed around said post of said bolt, said mating face defining a number of opposing radial splines for interdigitating engagement with the radial splines on said lower surface of said connector.

3. The system of claim 2 wherein the annular ring is integrally formed on the lower surface of said connector.

4. The system of claim 2 wherein the annular ring is a washer affixed to the lower surface of said connector.

5. A spinal fixation system comprising:

two paraellel rods, each having a first end and a second end;

a fixed rod connector having a lower surface and an upper surface and defining a thru-hole, said fixed rod connector fixed to the first end of both of said rods;

a dynamic rod connector having a lower surface and an upper surface and defining a thru-hole, said dynamic rod connector slidably engaged to each of said rods;

a number of spikes fixedly projecting from said lower surface of each of said connectors, said spikes configured to engage a vertebra;

one bolt for each connector, each said bolt having a vertebra engaging portion on a first end and a threaded post on a second end, said post insertable through said thru-holes of said connectors;

an integral flange between said vertebra engaging portion and said post for supporting said connector;

a threaded nut for each of said bolts, said nut engageable to a bolt to secure a connector to a bolt; and a locking mechanism configured to prevent each said bolt from rotating relative to said connector and the vertebra when said nut is being threaded onto said post.

6. The system of claim 5 wherein said locking mechanism includes:

an annular ring defined on the lower surface of said connector and concentrically disposed around the thru-hole, said annular ring defining a number of radial splines; and a mating face affixed to said flange and concentrically disposed around said post of said bolt, said mating face defining a number of opposing radial splines for interdigitating engagement with the radial splines on said lower surface of said connector.

7. The system of claim 6 wherein the annular ring is integrally formed on the lower surface of said connector.

8. The system of claim 6 wherein the annular ring is a washer affixed to the lower surface of said connector.

9. A transverse fixator assembly for spanning between a pair of longitudinal members situated adjacent a patient's vertebrae, comprising:

a number of connectors each having a lower bone engagement surface and an upper surface, each of said connectors configured to span a distance between said members and engageable to said members, each of said connectors defining a thru-hole for engaging a bone bolt; and a number of spikes projecting from said lower surface of each said connector, said spikes configured to engage a vertebra;

a bone bolt for each of said connectors, said bone bolt including,
a vertebra engaging portion on a first end,
a threaded post on a second end, said post insertable through said thru-hole of said connector, and
an integral flange between said vertebra engaging portion and said post for supporting said connector;

a threaded nut for each of said bolts, said nut engageable to a bolt to secure a connector to a bolt; and a locking mechanism configured to prevent the bolt from rotating relative to said connector and the vertebra when the threaded nut is being threaded onto said post.

10. The system of claim 9 wherein each of said thru-holes includes recesses defined in the upper surface of said connector and said nuts are sized to be received in a recess without extending above the upper surface.

11. The system of claim 9 wherein said locking mechanism includes:

an annular ring defined on the lower surface of said connector and concentrically disposed around the thru-hole, said annular ring including a number of radial splines;

a mating face affixed to said flange and concentrically disposed around said post of said bolt, said mating face having a number of opposing radial splines for interdigitating engagement with the radial splines on said lower surface of said connector.

12. The system of claim 11 wherein the annular ring is integrally formed on the lower surface of said connector.

13. The system of claim 11 wherein the annular ring is a washer affixed to the lower surface of said connector.

* * * * *